United States Patent [19]

Franke

[11] 4,035,650
[45] July 12, 1977

[54] DENTAL X-RAY DIAGNOSTIC INSTALLATION
[75] Inventor: Kurt Franke, Erlangen, Germany
[73] Assignee: Siemens Aktiengesellschaft, Berlin & Munich, Germany
[21] Appl. No.: 610,257
[22] Filed: Sept. 4, 1975
[30] Foreign Application Priority Data
Sept. 12, 1974 Germany .......................... 2443681
[51] Int. Cl.$^2$ ........................................ G03B 41/16
[52] U.S. Cl. ................................ 250/413; 250/479
[58] Field of Search .......... 250/401, 402, 408, 409, 250/413, 414, 416, 479

[56] References Cited
U.S. PATENT DOCUMENTS
2,946,892  7/1960  Bas-Taymaz .................... 250/479
3,854,096  12/1974  Hermeyer ........................ 250/402

Primary Examiner—Craig E. Church
Attorney, Agent, or Firm—Hill, Gross, Simpson, Van Santen, Steadman, Chiara & Simpson

[57] ABSTRACT

An X-ray diagnostic installation in which there is effectuated an automatic proportioning of the exposure time. In the dental X-ray exposure installation, a ray detector is applied to the pouch, which delivers an electrical signal in conformance with the ray intensity when it is impinged upon by X-radiation, and which is interconnected with the setting means to an automatic exposure timer in such a manner whereby the exposure time is determined by an output signal of the ray detector for the purpose of effectuating an optimum degree of film darkening.

2 Claims, 3 Drawing Figures

DENTAL X-RAY DIAGNOSTIC INSTALLATION

FIELD OF THE INVENTION

The present invention relates to a dental X-ray diagnostic installation.

DISCUSSION OF THE PRIOR ART

In a known X-ray diagnostic installation for dental purposes which includes an X-ray generator having setting or adjusting means associated therewith for the proportioning of the exposure time, and a pouch with an X-ray film which may be applied to the face of a patient, it is possible to produce tooth condition exposures in which the hollow anode of an X-ray tube is introduced into the mouth of the patient, and the pouch containing the X-ray film is externally applied against the face of the patient. Hereby, the exposure time is determined through a timing switch, the latter of which is manually adjusted. The correct light exposure for a tooth condition exposure thus depends upon the correct feel or sense of the operating personnel for the X-ray diagnostic installation.

SUMMARY OF THE INVENTION

Accordingly, it is an object of the present invention to provide an X-ray diagnostic installation of the above-mentioned type, in which there is effectuated an automatic proportioning of the exposure time.

The foregoing object is inventively achieved in that in the above-mentioned dental X-ray exposure installation, a ray detector is applied to the pouch, which delivers an electrical signal in conformance with the ray intensity when it is impinged upon by X-radiation, and which is interconnected with the setting means to an automatic exposure timer in such a manner whereby the exposure time is determined by an output signal of the ray detector for the purpose of effectuating an optimum degree of film darkening.

The invention is predicated on the knowledge that the known automatic exposure timers in larger X-ray installations by means of which the exposure time is automatically determined, can also be readily transposed to dental X-ray diagnostic installations with adjustable exposure time, when the ray detector is applied to the film pouch.

In a suitable construction of the invention, the ray detector is divided into a row of measuring fields or areas which are located proximate one edge of the pouch, and wherein the automatic exposure timer incorporates means for the selection of the presently desired measuring area. This construction allows the present image area, in which the image should possess an optimum degree of film darkening, to be selected by means of the measuring areas.

BRIEF DESCRIPTION OF THE DRAWINGS

Further advantages and details of the invention may now be ascertained from the following description of an exemplary embodiment thereof, taken in conjunction with the accompanying drawings; in which.

DETAILED DESCRIPTION

Figure 1:
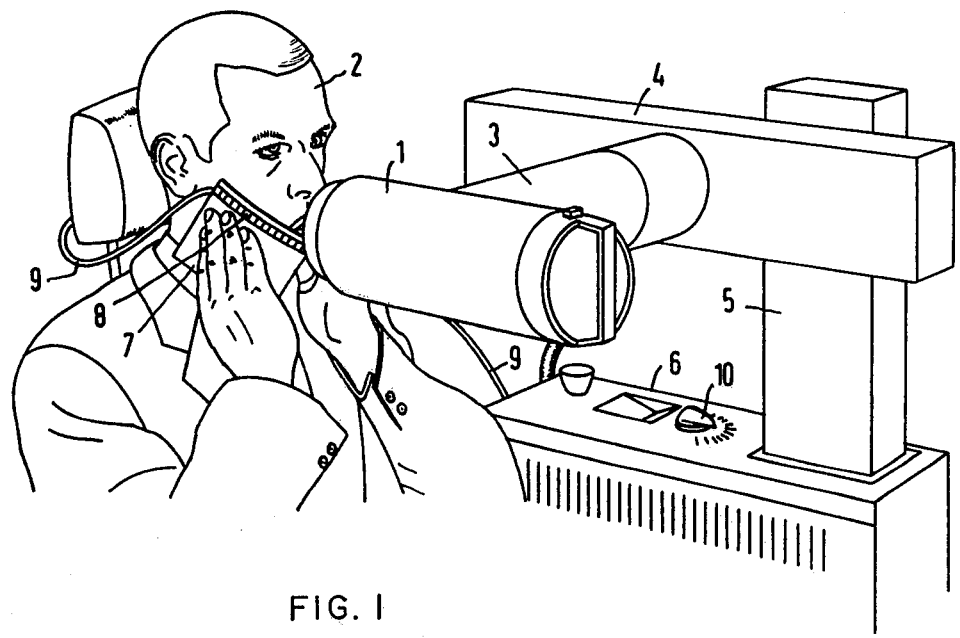
FIG. 1 illustrates a perspective view of a dental X-ray diagnostic installation constructed pursuant to the invention.

Referring now to the drawings, there is shown a dental X-ray diagnostic installation which contains an X-ray tube in a housing 1, with the hollow anode of the tube being introducible into the mouth of a patient 2. The housing 1 is supported, through the intermediary of an arm 3, on a carrier 4 which is connected with an upright or column 5 so as to be vertically adjustable. The column 5 is fastened to an apparatus housing 6 within which there are located the electrical construction elements associated with the X-ray tube 1.

The X-ray film is located in a film pouch 7 which, for example, may be constituted of a plastic material. Arranged on the exterior of the film pouch 7, in effect, viewed in the ray direction behind the X-ray film, is a ray detector 8 which consists of a plurality of measuring areas which are located in a row. The ray detector 8 is connected through the intermediary of a cable 9 with the electrical components in apparatus housing 6.

A switch 10 is located on the apparatus housing 6, which facilitates the selection of one of the measuring areas of the ray detector, and whose output signal is to be processed. The measuring area is thereby so selected that a desired region of the X-ray film evidences an optical film darkening. The presently selected measuring area of the ray detector 8 delivers an electrical signal when it is impinged upon by the X-radiation, which corresponds to the radiation intensity. The ray detector 8 is interconnected with the setting means for the exposure time in the X-ray apparatus to an automatic exposure timer. The exposure time is determined hereby in that the output signal of the ray detector 8 is intergrated in a known manner, and after the reaching of a predetermined integral which corresponds to a predetermined radiation dosage on the desired measuring area, there follows a switching off of the X-radiation.

The ray detector 8 suitably is located along the edge of the pouch 7 so that its measuring areas, upon application of the pouch against the face of the patient, lie opposite the teeth which are to be X-rayed. Illustrated in the drawing is an upper molar exposure. For a lower molar exposure, the pouch 7 must be rotated through an angle of 180° so that the ray detector 8 is then located along the lower edge of the pouch 7.

Within the scope of the invention, there may be provided on the apparatus housing 6, in a known manner, setting means for effecting the correlation of the automatic exposure timer to the film sensitivity and to the object density or thickness.

Figure 2:
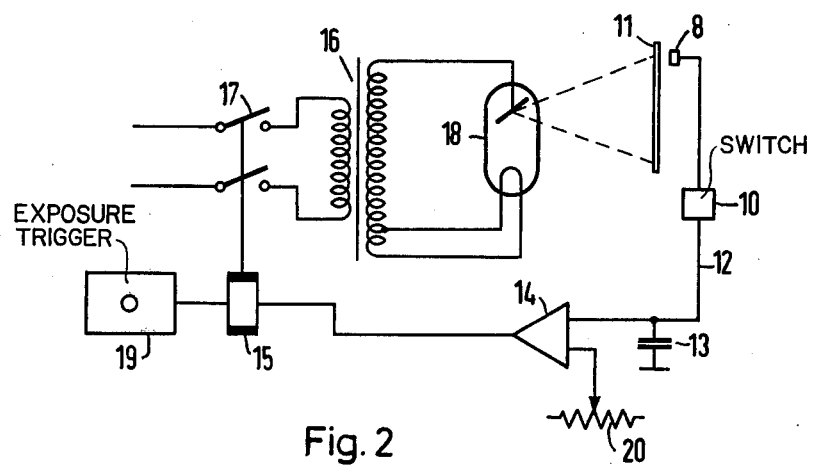
FIG. 2 shows a schematic circuit diagram for an automatic exposure timer utilized in the installation of FIG. 1.

FIG. 2 illustrates a schematic circuit diagram for the automatic exposure timer. The ray detector 8, which is located behind the X-ray film 11 as viewed in the ray direction, is connected through an integrating condenser 13 through a conductor 12. The voltage which is applied to the integrating condenser 13 is transmitted to a first input of a comparator 14, at whose other input there is applied a reference signal which is tapped off at a reference setting means 20. The comparator 14 controls a relay 15 which actuates two contacts 17 positioned in the primary circuit of a high-voltage transformer 16. The X-ray tube is schematically shown in FIG. 2 and is designated by reference numeral 18.

As soon as the voltage at condenser 13 reaches the signal tapped off at the reference setting means 20, the comparator 14 causes the relay 15 to open its contacts 17, which are closed during the taking of an exposure. The timepoint at which the contacts 17 are opened depends upon as to how rapidly the output signal of the ray detector 8 reaches the voltage which is tapped off at the reference setting means 20. In order to commence an exposure, the relay 15 is excited through an exposure trigger 19, so that its contacts 17 are closed at the beginning of an exposure.

Figure 3:
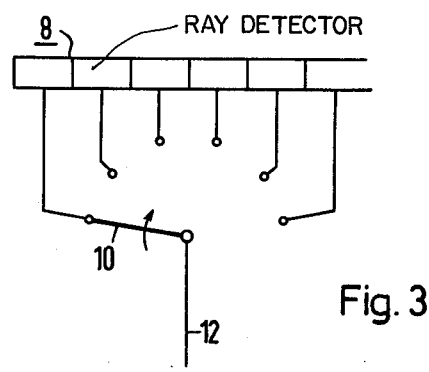
FIG. 3 schematically illustrates a rotary switch which is employed in the circuit diagram of FIG. 2.

FIG. 3 diagrammatically illustrates the switch 10, which may be a rotary switch. The rotary switch 10 is located between the conductor 12 and the ray detector 8, and presently connects one measuring area of the ray detector 8 with the conductor 12. The switch 10 is illustrated only schematically in FIG. 2 of the drawings.

While there has been shown what is considered to be the preferred embodiment of the invention, it will be obvious that modifications may be made which come within the scope of the disclosure of the specification.

What is claimed is:

1. In a dental X-ray diagnostic installation including an X-ray generator and a film retaining pouch adapted to be placed on the face of a patient, the improvement comprising:

ray detector means having a plurality of measuring areas arranged in a row and mounted on and carried by the pouch for delivering an electrical output signal conforming to the intensity of X-radiation impinged on each of said measuring areas;

each of said measuring areas having an effective area, approximating the size of a local tooth area to be X-rayed;

switch means for selecting one of said measuring areas of the ray detector; and control means electrically interconnecting said generator through the switch means to a selected one of the measuring areas of said ray detector means and effective to discontinue operation of said generator upon receipt of a predetermined electrical output signal from said one of said measuring areas of said ray detector means corresponding to an X-ray exposure sensed by the detector means on the pouch for attaining an optimum degree of darkening of the film contained within the pouch immediately adjacent said one measuring area.

2. A dental X-ray diagnostic installation as recited in claim 1, wherein the control means comprises:

a variable resistor, a comparator, said variable resistor applying a reference voltage to one input of said comparator, said comparator having a second input connected by the switch means to said one of said measuring areas of said ray detector means, relay means with an electromagnetic coil having one terminal connected to the output of said comparator, a trigger switch, a second terminal of said coil being connected to said trigger switch, said relay means having contacts opening the circuit of said X-ray generator for terminating the exposure when said relay means is acutated.

* * * * *